United States Patent [19]

Tonne et al.

[11] 4,306,074

[45] Dec. 15, 1981

[54] PREPARATION OF A MIXTURE OF AN ALKYL 3-CHLOROANTHRANILATE AND AN ALKYL 6-CHLOROANTHRANILATE

[75] Inventors: Peter Tonne, Neustadt; Heinz-Guenter Oeser, Ludwigshafen; Dietrich Mangold, Neckargemuend, all of Fed. Rep. of Germany

[73] Assignee: BASF Aktiengesellschaft, Fed. Rep. of Germany

[21] Appl. No.: 153,576

[22] Filed: May 27, 1980

[30] Foreign Application Priority Data

Jun. 20, 1977 [DE] Fed. Rep. of Germany ....... 2924789

[51] Int. Cl.$^3$ ............................................. C07C 101/54
[52] U.S. Cl. .......................................... 560/47; 544/94
[58] Field of Search ........................................... 560/47

[56] References Cited

U.S. PATENT DOCUMENTS

| | | |
|---|---|---|
| 3,184,462 | 5/1965 | Scarborough et al. |
| 3,758,437 | 9/1973 | Adams ................................. 560/47 |
| 4,082,749 | 4/1978 | Quadbeck-Seeger et al. |
| 4,135,050 | 1/1979 | Hess et al. ............................ 560/47 |

FOREIGN PATENT DOCUMENTS

| | | |
|---|---|---|
| 107505 | 11/1899 | Fed. Rep. of Germany . |
| 127138 | 12/1901 | Fed. Rep. of Germany . |
| 2357749 | 5/1975 | Fed. Rep. of Germany . |

OTHER PUBLICATIONS

Wagner et al., Synthetic Organic Chemistry, John Wiley & Sons, Inc., N.Y., pp. 482 & 567-568, 1953.
Müller, Houben-Weyl, Methoden der Organischen Chemie, vol. XI/I, pp. 854-862 (1971).
Foerst, Ullmanns Encyklopadie der Technischen Chemie, vol. 13, pp. 723-733, 1962.
Cahn, J. Chem. Soc., p. 2407, 1957.
Coleman, J. Organic Chemistry, 24, pp. 1214-1219, 1959.
Müller, Houben-Weyl, Methoden der Organischen Chemie, vol. 8, pp. 516-549, 1952.
Sijthoff, Rec. Trau. Chim. Pay-Bas, 32, p. 283 (1913).

*Primary Examiner*—G. T. Breitenstein
*Attorney, Agent, or Firm*—Keil & Witherspoon

[57] ABSTRACT

A mixture of an alkyl 3-chloroanthranilate and an alkyl 6-chloroanthranilate, with a particular molar ratio of the components, is prepared by (a) reacting 3-chlorophthalic anhydride with ammonia, an alkali metal hydroxide and an alkali metal hypochlorite or (b) converting 3-chlorophthalic anhydride to 3-chlorophthalimide followed by reaction of the latter with an alkali metal hydroxide and an alkali metal hypochlorite, and, finally, esterifying the mixture of 5-chloroisatoic anhydride and 8-chloroisatoic anhydride, obtained by method (a) or method (b), with an alkanol.

The compounds obtainable by the process of the invention are valuable starting materials for the preparation of dyes, crop protection agents and scents.

14 Claims, No Drawings

PREPARATION OF A MIXTURE OF AN ALKYL 3-CHLOROANTHRANILATE AND AN ALKYL 6-CHLOROANTHRANILATE

The present invention relates to a process for the preparation of a mixture of an alkyl 3-chloroanthranilate and an alkyl 6-chloroanthranilate, in a particular molar ratio of the components, by a) reacting 3-chlorophthalic anhydride with ammonia, an alkali metal hydroxide and an alkali metal hypochlorite or b) converting 3-chlorophthalic anhydride to 3-chlorophthalimide followed by reaction of the latter with an alkali metal hydroxide and an alkali metal hypochlorite, and, finally, esterifying the mixture of 5-chloroisatoic anhydride and 8-chloroisatoic anhydride, obtained by method a) or method b), with an alkanol.

Houben-Weyl, Methoden der Organischen Chemie, Volume XI/1, pages 854–862, discloses that carboxylic acid amides can be converted to primary amines by a Hofmann degradation with bromine or chlorine and an alkali. Further, Ullmanns Encyklopädie der technischen Chemie, Volume 13, pages 723–733, and German Patent No. 127,138, disclose that phthalic anhydride can be converted to phthalimide by means of ammonia and that isatoic anhydride can be prepared from the phthalimide by reaction with a hypohalite in alkaline solution. Hitherto, these methods, and the esterification of the resulting isatoic anhydrides, have neither been used, nor described, for the preparation of alkyl 3-chloroanthranilates.

3-Chloroanthranilic acid is in the main prepared by reacting o-chloroaniline with chloral hydrate and hydroxylamine hydrochloride to give o-chloroisonitrosoacetanilide, then reacting the anilide with sulfuric acid to give 7-chloroisatin, and subsequently reacting the latter with hydrogen peroxide. The disadvantage of this method of synthesis is on the one hand the large number of steps involved and on the other hand the large amount of extraneous salts which are produced at the o-chloroisonitrosoacetanilide stage and which pollute the environment. The esterification of 3-chloroanthranilic acid furthermore gives unsatisfactory yields.

The synthesis of 6-chloroanthranilic acid by this method gives, at the isatin stage, an isomer mixture of 4- and 6-chloroisatin (U.S. Pat. No. 3,184,462), from which the desired 4-chloroisatin can only be obtained by an expensive separating operation, the yield being 45 percent.

J. Chem. Soc. 1957, page 2,407 describes a process for the preparation of 6-chloroanthranilic acid by oxidizing 2-chloro-6-nitrotoluene with alkali metal permanganate and then reducing the 2-chloro-6-nitrobenzoic acid with iron sulfate and aqueous ammonia. However, in this synthesis the yields (60% for the oxidation and 77% for the reduction) are again unsatisfactory. Equally, there is no method of synthesis of 2-chloro-6-nitrotoluene which is satisfactory when operated industrially, since both the chlorination of o-nitrotoluene (German Patent No. 107,505) and the nitration of o-chlorotoluene (Rec. Trav. Chim. Pay-Bas 32 (1913), 283) give this compound in yields of less than 30%.

We have found that a mixture of an alkyl 3-chloroanthranilate of the formula

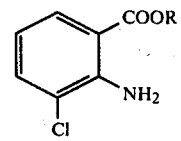

and an alkyl 6-chloroanthranilate of the formula

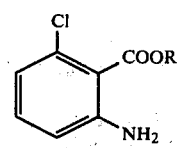

where R is alkyl, in a ratio of from 2.9 to 3.1 moles of the one ester to one mole of the other ester, may be prepared advantageously by a method wherein (a 1) 3-chlorophthalic anhydride is reacted with ammonia and an alkali metal hypochlorite in the presence of an alkali metal hydroxide at from 0° to 100° C., and thereafter (a 2) the resulting mixture of 8-chloroisatoic anhydride of the formula

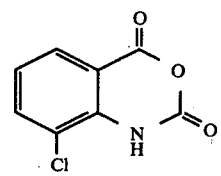

and 5-chloroisatoic anhydride of the formula

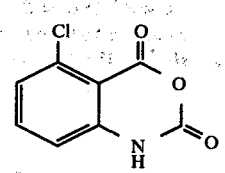

is esterified with an alkanol of the formula

ROH     III where R has the above meaning, in the presence of an esterification catalyst, or (b 1) 3-chlorophthalic anhydride is reacted with ammonia or formamide and thereafter (b 2) the resulting 3-chlorophthalimide is reacted with an alkali metal hypochlorite in the presence of an alkali metal hydroxide at from 0° to 100° C., after which (b 3) the resulting mixture of 8-chloroisatoic anhydride of the formula

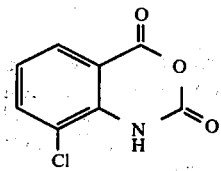

and 5-chloroisatoic anhydride of the formula

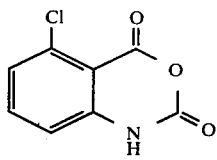 IIb is esterified with an alkanol of the formula

ROH                       III where R has the above meaning, in the presence of an esterification catalyst.

Where methanol and sodium hypochlorite are used, the reaction can, in the case of process a (a 1+a 2) be represented by the following equations:

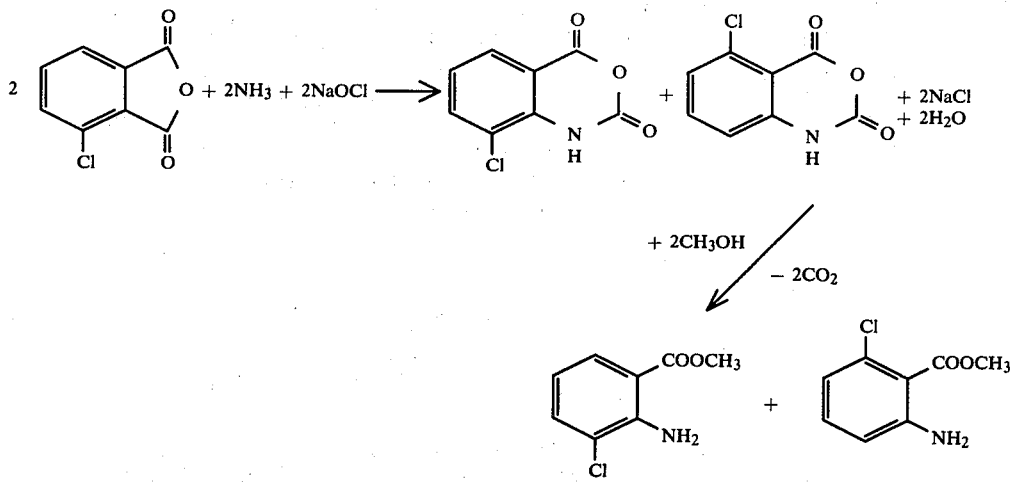

Where formamide, methanol and sodium hypochlorite are used, the reaction can, in the case of process b (b 1+b 2+b 3), be represented by the following equations:

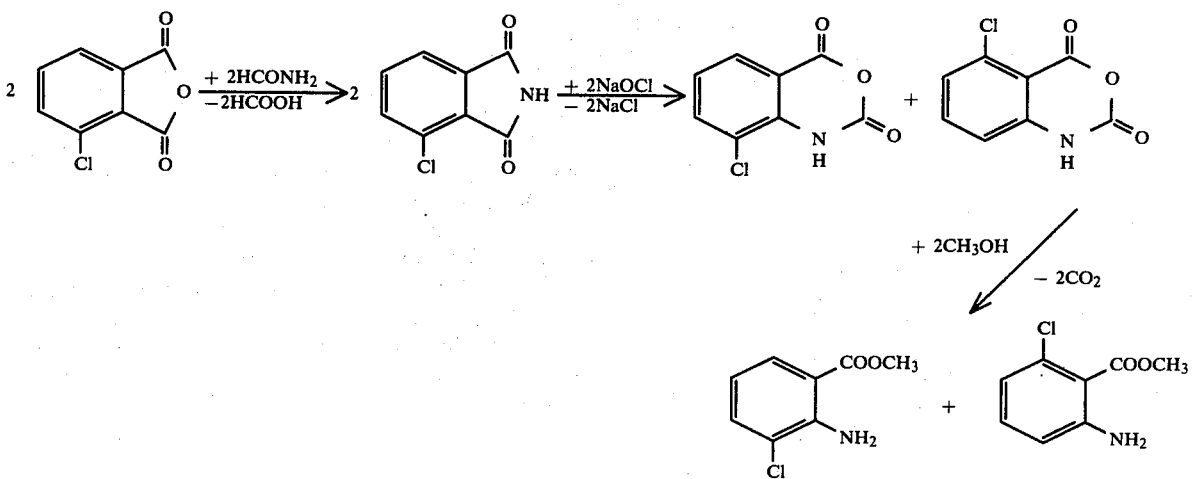

Compared to the conventional processes, the process according to the invention starts from a more easily prepared starting material, namely 3-chlorophthalic anhydride or 3-chlorophthalimide, and gives specific mixtures of alkyl 3-chloroanthranilate and alkyl 6-chloroanthranilate, from which the individual components of the mixtures may be obtained, more simply and more economically, and in some cases with better yield and greater purity. Using method a), the alkyl 3-chloroanthranilate, especially methyl 3-chloroanthranilate, is obtained as the main product and the alkyl 6-chloroanthranilate, especially methyl 6-chloroanthranilate, as a by-product, whilst using method b) the alkyl 6-chloroanthranilate, especially methyl 6-chloroanthranilate, is obtained as the main product and the alkyl 3-chloroanthranilate, especially methyl 3-chloroanthranilate, as a by-product. However, in both cases, the process according to the invention gives a mixture with a defined ratio of main product to by-product. All these advantageous results of the novel process are surprising in view of the prior art. Because of the reactive chlorine substituents and the reactants in both method a) and mwethod b), a substantially poorer yield, and/or the formation of heterogeneous mixtures, would have been expected. It is also surprising, in view of the prior art, that a well-defined isomer ratio is obtainable by the novel process and hence both end products can be successively prepared as the main product in the same plant, without a substantial change in operation. The novel process is therefore also of interest for the preparation of both end products individually, since they can be obtained by separating the mixtures by simple distillation. In addition, method b), using formamide, offers the possibility of preparing an ammonia-free phthalimide in an advantageous manner and in excellent yields; this is of importance when the end products are used in syntheses which are sensitive to ammonia.

In method a 1) and b 1), the reaction is advantageously carried out in a stoichiometric ratio or with an excess of ammonia or, in the case of b 1) an excess of formamide, advantageously with a molar ratio of from 1 to 20, preferably from 1 to 5, especially from 1 to 1.5, moles of ammonia or formamide per mole of phthalic anhydride. The reaction in stage b 1) may be carried out continuously or batchwise, under atmospheric or superatmospheric pressure, advantageously at from 80° C. to 300° C., preferably at from 100° to 180° C. It is possible to use pure 3-chlorophthalic anhydride, though on an industrial scale it is simpler and more economical to use technical-grade crude 3-chlorophthalic anhydride, for example a material containing from 90 to 95 percent by weight of pure 3-chlorophthalic anhydride. Equally, the ammonia may be pure or may be mixed with an inert gas, for example nitrogen or carbon dioxide. The reaction in stage b 1) may be carried out as follows: the 3-chlorophthalic anhydride and ammonia or formamide are reacted with one another at the reaction temperature, and the 3-chlorophthalimide is then isolated from the reaction mixture in a conventional manner, for example by mixing with water, and filtering the mixture.

The other starting materials used are hypochlorites in an aqueous medium, as a rule in the form of aqueous alkaline solutions. Advantageously, the phthalic acid derivative is used in the form of an aqueous solution or suspension containing from 1 to 50 percent by weight of 3-chlorophthalic anhydride (method a 1) or of 3-chlorophthalimide (method b 2). The aqueous hypochlorite solutions in general contain from 5 to 15, preferably from 12 to 14, percent by weight of hypochlorite and may in addition contain from 0.2 to 2.5 moles, preferably from 1 to 2.1 moles, of alkali metal hydroxide per mole of hypochlorite. This amount of alkali metal hydroxide does not include any alkali present in the catalyst or hypochlorite or alkali bonded to the catalyst. The mixture of all starting materials for stage a 1) or b 2) in general contains a total of from 0.9 to 1.5, preferably from 0.95 to 1.1, moles of hypochlorite and, advantageously, a total of from 0.9 to 3 moles, preferably from 1 to 2.1 moles, of alkali metal hydroxide not including the alkali metal cations of the hypochlorite compound per mole of 3-chlorophthalic anhydride or 3-chlorophthalimide. If the aqueous hypochlorite solution does not contain any free alkali metal hydroxide, it is advantageous to add from 0.2 to 2, preferably from 1 to 2, moles of alkali metal hydroxide, per mole of hypochlorite, at the start of, or during, the reaction. The preferred alkali metal hypochlorites are sodium hypochlorite and potassium hypochlorite and the preferred alkali metal hydroxides are sodium hydroxide and potassium hydroxide. In method a 1) it is also possible first to add ammonia, then the alkali metal hydroxide, in a single shot or in portions, and, last of all, the hydrochlorite; in that case, it is again advantageous to use the amounts of ammonia and/or alkali metal hydroxide mentioned above.

Suitable catalysts for stage a 1) or b 2) are bromine, iodine and/or amides of the formula

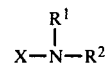

where $R^1$ is a sulfonic acid group, a sulfonate radical or a sulfonamide group, $R^2$ is hydrogen, an aliphatic radical, chlorine or bromine, X is chlorine, bromine or hydrogen, $R^1$ and $R^2$ may also, conjointly with the adjacent nitrogen, be members of a heterocyclic radical which contains, adjacent to the nitrogen, one or more sulfone groups or phosphonyl groups of the formula

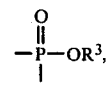

where $R^3$ is hydrogen or an alkali metal atom, and $R^1$ and $R^2$ together may also be

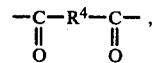

where $R^4$ is alkylene or

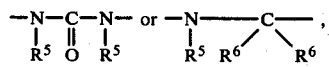

$R^5$ is hydrogen, chlorine or bromine and $R^6$ is an aliphatic radical. In general these catalysts are used in an amount of from 0.0001 to 0.1, preferably from 0.001 to 0.01, mole per mole of 3-chlorophthalic anhydride or 3-chlorophalimide. Instead of the catalysts mentioned, it is also possible to use compounds which form these catalysts under the reaction conditions, for example to use bromides or iodides instead of bromine or iodine. In that case, the water-soluble halide is preferred. These halides are advantageously the alkaline earth metal halies or especially the alkali metal halides, for example calcium bromide, calcium iodide, magnesium bromide, magnesium iodide, lithium bromide, lithium iodide and, in particular, sodium bromide, sodium iodide, potassium bromide and potassium iodide.

Preferred haloamides IV are those where $R^1$ is a sulfinic acid group, a sulfonate radical, especially an alkali metal sulfonate radical such as a sodium sulfonate radical or potassium sulfonate radical, or a sulfonamide group, $R^2$ is chlorine, bromine, alkyl of 1 to 4 carbon atoms or, in particular, hydrogen, X is bromine, chlorine or, advantageously, hydrogen, $R^1$ and $R^2$ may also, conjointly with the adjacent nitrogen, be members of a heterocyclic 5-membered or 6-membered ring which contains, adjacent to the nitrogen, one or more sulfone groups or phosphonyl groups of the formula

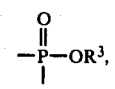

where $R^3$ is hydrogen or an alkali metal atom, especially sodium or potassium, or $R^1$ and $R^2$ together may be

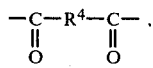

where $R^4$ is alkylene of 2 to 4 carbon atoms,

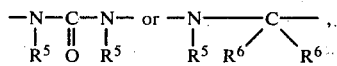

$R^5$ is hydrogen, chlorine or bromine and $R^6$ is alkyl of 1 to 4 carbon atoms, especially methyl. In addition, a phenylene nucleus may be fused to the above heterocyclic ring. Advantageously, the heterocyclic radical contains 2 sulfone or phosphonyl groups adjacent to the nitrogen, or two or three sulfonamido groups or phosphonamido groups, the groups being, in particular, in one and the same ring where a polynuclear heterocyclic radical is concerned. The above preferred radicals may in addition be substituted by groups or atoms which are inert under the reaction conditions, for example chlorine, bromine or alkyl of 1 to 4 carbon atoms, or carboxyl or carboxylate groups as substituents of the phenyl nucleus.

Examples of suitable catalysts are glutarimide, adipimide and succinimide and, preferably, cyanuric acid, 5,5-dimethylhydantoin, trisulfamide, N-methyl-sulfamic acid and sodium triimidometaphosphate, as well as mixtures of the above compounds IV; particularly preferred catalysts are, however, sulfamic acid and its salts, advantageously the alkali metal salts, such as the sodium salt or potassium salt, and sulfamide, which may or may not be mixed with the above amides IV.

If desired, the polymerization inhibitors described in German Laid-Open Application DOS No. 2,357,749 may also be used as catalysts for step a 1) or b 2), advantageously following the method described in the said DOS.

In method a 1) or b 2), the reaction is carried out continuously or batchwise, at from 0° to 100° C., preferably from 10° to 85° C., under atmospheric or superatmospheric pressure. Reaction a 1) or b 2) may be carried out as follows: An aqueous solution of the hypohalite is introduced into a mixture of 3-chlorophthalic anhydride and ammonia (or 3-chlorophthalimide without ammonia), catalyst, alkali metal hydroxide and water, which may or may not contain an anti-foam agent, and the mixture is kept at the reaction temperature for from 1 to 4,000 seconds. The end product is then isolated in a conventional manner, for example by neutralizing the reaction mixture with a suitable acid, such as sulfuric acid, and filtering.

It is also possible to add the catalyst, advantageously mixed with water, to the starting mixture either separately or together with the hypohalite. In a preferred embodiment, which at the same time illustrates the particularly simple and advantageous manner in which the process according to the invention may be operated in practice, 3-chlorophthalic anhydride and ammonia, with or without alkali metal hydroxide, are first reacted, as a rule at from 20° to 80° C., the hypochlrite is added directly and rapidly, advantageously in one shot, into the resulting reaction mixture over from 1 to 100 seconds, and the batch is them immediately neutralized with acid.

In stage a 1), the resulting mixture of chloroisatoic anhydrides, and correspondingly in stage a 2) the resulting mixture of alkyl chloroanthranilates, contains from 2.9 to 3.1, preferably from 2.95 to 3.05, moles of 8-chloroisatoic anhydride or alkyl 3-chloroanthranilate per mole of 5-chloroisatoic anhydride or alkyl 6-chloroanthranilate; in stage b 2) the resulting mixture of chloroisatoic anhydrides and correspondingly in stage b 3) the resulting mixture of alkyl chloroanthranilates, contains from 2.9 to 3.1, preferably from 2.95 to 3.05, moles of 5-c hloroisatoic anhydride or alkyl 6-chloroanthranilate per mole of 8-chloroisatoic anhydride or alkyl 3-chloroanthranilate respectively.

In stage a 2) or b 3), the mixture of 5-chloroisatoic anhydride and 8-chloroisatoic anhydride is reacted with the alkanol III in stoichiometric amount or in excess, preferably using from 1 to 50, especially from 1 to 30, moles of alkanol III per mole of 5-chloroisatoic anhydride and 8-chloroisatoic anhydride. Preferred alkanols III and accordingly preferred alkyl chloroanthranilates Ia and Ib are those where R is alkyl of 1 to 18, advantageously of 1 to 8, especially of 1 to 4, carbon atoms. Specific examples of suitable alkanols are ethanol, n-propanol, isopropanol, butanol, isobutanol, sec.-butanol, tert.-butanol, pentanol, 2,2-dimethylpropanol, 2-ethylhexanol, hexanol, heptanol, octanol, 2-ethyloctanol and, preferably, methanol. The reaction is as a rule carried out at from 10° to 170° C., preferably from 20° to 90° C., under atmospheric or superatmospheric pressure, and continuously or batchwise. Advantageous catalysts to use are acids, e.g. phosphoric acid, aromatic sulfonic acids, such as p-toluenesulfonic acid, or, in particular, hydrogen chloride and sulfuric acid; in particular, it is advantageous to use from 0.5 to 15, especially from 3 to 10, percent by weight of acid, based on starting materials IIa and IIb. Compounds which bind the water formed, for example anhydrous salts, e.g. copper sulfate or iron sulfate, may or may not be used in addition. Esterification catalysts such as acid chlorides, e.g. thionyl chloride, chlorosulfonic acid or ansolvo-acids, e.g. boron trifluoride, or special esterification operations, for example esterification accompanied by azeotropic distillation using, for example, benzene or toluene, may also be employed.

Other preferred catalysts are bases, as a rule tertiary amines, e.g. trimethylamine, triethylamine, tripropylamine, triisopropylamine, tributylamine, trisobutylamine, tri-sec.-butylamine, tri-tert.-butylamine, tribenzylamine, tricyclohexylamine, triamylamine, trihexylamine, N,N-dimethylaniline, N,N-diethylaniline, N-methylpiperidine, N-ethylpiperidine, N-methylpyrrolidine, N-ethylpyrrolidine, N-methylimidazole, N-ethylimidazole, N-methylpyrrole, N-ethylpyrrole, N-methylmorpholine, N-ethylmorpholine, N-methylhexamethyleneimine, N-ethylhexamethyleneimine and pyridine. When these are used, the reaction is advantageously carried out with from 0.01 to 0.5, preferably from 0.05 to 0.35, equivalent of basic compound per mole of starting material IIa and IIb. Alkali metal hydroxides or alkali metal carbonates may also be used as catalysts, for example by the method described in J. Org. Chem., 24 (1959), -b 1,214–1,219.

The reaction in stage a 2) or b 3) may be carried out as follows: a mixture of the starting materials IIa, IIb and III, and an acid or base as the esterification catalyst is kept at the above temperature for from 1 to 12 hours, whilst stirring. The ester I is then isolated in a conventional manner, for example by fractional distillation. Regarding the details of the esterification reaction, reference may be made to Houben-Weyl, Methoden der Organischen Chemie, Volume 8, pages 516-549.

The compounds Ia and Ib obtainable by the process of the invention are valuable starting materials for the preparation of dyes, crop protection agents and scents. Regarding their use, reference may be made to the above publications.

In the Examples which follow, parts are by weight and bear the same relation to parts by volume as that of the kilogram to the liter.

EXAMPLE 1

(a 1) 6,800 parts of 3-chlorophthalic anhydride are stirred into 70,000 parts by volume of water and 6,480 parts by volume of 21 percent strength by weight ammonia at 30° C., resulting in a pH of 5.3. The mixture is then brought to pH 10 with 50 percent strength by weight sodium hydroxide solution, after which 4,300 parts by volume of 50 percent strength by weight sodium hydroxide solution and a further 6,800 parts of 3-chlorophthalic anhydride are added. The mixture is stirred for a further 4 hours, after which 250 parts of triisobutyl phosphate, 150 parts of sulfamic acid and a further 100 parts of 3-chlorophthalic anhydride are added. The pH of the solution is then brought to 10 with 50 percent strength by weight sodium hydroxide solution, after which the mixture is cooled to 3° C. A solution of 60,000 parts by volume of water and 32,000 parts by volume of 13.4 percent strength by weight sodium hypochlorite solution is added to the preceding solution while increasing the temperature to 5° C. over 45 seconds, with vigorous stirring. The pH rises to 12.5. The mixture is then brought to pH 7 with 25 percent strength by weight sulfuric acid, heated to 30° C. and kept at pH 7 by further addition of 25 percent strength by weight sulfuric acid. 2.5 hours after the first addition of acid, the precipitate which has formed is filtered off, washed with water and dried under reduced pressure. 11,045 parts (77% of theory) of a mixture of 8-chloroisatoic anhydride and 5-chloroisatoic anhydride in the ratio of 3:1 are obtained; the mixture melts at 210°-218° C.

(a 2) A suspension of 26,700 parts of a 3:1 mixture of 8-chloroisatoic anhydride and 5-chloroisatoic anhydride in 150,000 parts by volume of methanol is heated to the reflux temperature. 5,000 parts by volume of triethylamine are then added over 2 hours, resulting in a steady evolution of carbon dioxide. The mixture is then refluxed for one hour, after which the alcohol is distilled off under reduced pressure and the residue is fractionated under reduced pressure. 15,220 parts (60.7% of theory) of methyl 3-chloroanthranilate, boiling point 100° C./0.3 mbar, and 5,066 parts (20.2% of theory) of methyl 6-chloroanthranilate, boiling point 117° C./0.3 mbar, are obtained.

EXAMPLE 2

(b 1) 300 parts of 3-chlorophthalic anhydride in 1,200 parts by volume of formamide are stirred for 2 hours at 140° C. The mixture is then allowed to cool to 100° C. after which the solution is poured into 5,000 parts by volume of water. The precipitate which forms is filtered off, washed with water and dried under reduced pressure. 275 parts (92.2% of theory) of 3-chlorophthalimide, of melting point 236°-238° C., are obtained.

(b 2) one part of sulfamic acid and 3 parts by volume of triisobutyl phosphate are added to a 3-chlorophthalimide solution (consisting of 182 parts of 3-chlorophthalimide, 2,500 parts by volume of water and 82 parts of 50 percent strength by weight sodium hydroxide solution). A solution of 550 parts of 13.4 percent strength by weight sodium hypochlorite solution in 800 parts by volume of water is added in one shot at 5° C., with vigorous stirring. 10 seconds after the start of the addition of the hypochlorite, the mixture is brought to pH 7 by adding 25 percent strength by weight sulfuric acid, and is then kept at pH 7 by further addition of acid. 1.5 hours after the first addition of acid, the precipitate which has formed is filtered off, washed with water and dried under reduced pressure at 60° C. 174 parts by weight (88% of theory) of a mixture of 8-chloroisatoic anhydride and 5-chloroisatoic anhydride in the ratio of 1:3 are obtained; the mixture melts, with decomposition, at 244°-246° C.

(b 3) A suspension of 500 parts of a 1:3 mixture of 8-chloroisatoic anhydride and 5-chloroisatoic anhydride in 2,000 parts by volume of methanol is reacted, similarly to Example 1 a 2), with 25 parts by volume of triethylamine, to give a methyl chloroanthranilate mixture. 96 parts (20.4% of theory) of methyl 3-chloroanthranilate, boiling point 100° C./0.3 mbar, and 288 parts (61.3% of theory) of methyl 6-chloroanthranilate, boiling point 117° C./0.3 mbar, are obtained.

We claim:

1. A process for the preparation of a mixture of an alkyl 3-chloroanthranilate of the formula

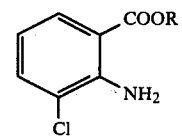

Ia and an alkyl 6-chloroanthranilate of the formula

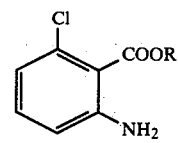

Ib where R is alkyl, in a ratio of from 2.9 to 3.1 moles of the one ester to one mole of the other ester, wherein (a 1) 3-chlorophthalic anhydride is reacted, optionally in the presence of a catalyst selected from the group consisting of bromine, bromides, iodine, iodides and/or an amide of the formula

IV where $R^1$ is a sulfonic acid group, a sulfonate radical or a sulfonamide group, $R^2$ is hydrogen, an aliphatic radical, chlorine or bromine, X is chlorine, bromine or hydrogen, $R^1$ and $R^2$ may also, conjointly with the adjacent nitrogen, be members of a heterocyclic radical which contains, adjacent to the nitrogen, one or more sulfone groups or phosphonyl groups of the formula

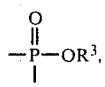

where $R^3$ is hydrogen or an alkali metal atom, and $R^1$ and $R^2$ together may also be

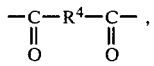

where $R^4$ is alkylene or

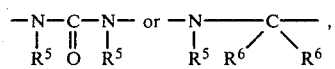

$R^5$ is hydrogen, chlorine or bromine and $R^6$ is an aliphatic radical, with ammonia and an alkali metal hypochlorite in the presence of an alkali metal hydroxide at from 0° to 100° C., and thereafter (a 2) the resulting mixture of 8-chloroisatoic anhydride of the formula

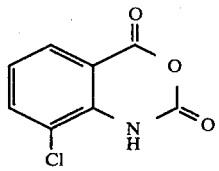

IIa and 5-chloroisatoic anhydride of the formula

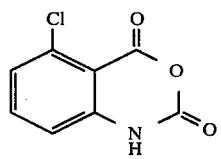

IIb is esterified with an alkanol of the formula

ROH                         III where R has the above meaning, in the presence of an esterification catalyst, or (b 1) 3-chlorophthalic anhydride is reacted with ammonia or formamide and thereafter (b 2) the resulting 3-chlorophthalimide is reacted, optionally in the presence of a catalyst selected from the group consisting of bromine, bromides, iodine, iodides and/or an amide of the formula

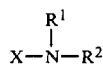

IV where $R^1$ is a sulfonic acid group, a sulfonate radical or a sulfonamide group, $R^2$ is hydrogen, an aliphatic radical, chlorine or bromine, X is chlorine, bromine or hydrogen, $R^1$ and $R^2$ may also, conjointly with the adjacent nitrogen, be members of a heterocyclic radical which contains, adjacent to the nitrogen, one or more sulfone groups or phosphonyl groups of the formula

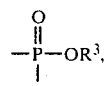

where $R^3$ is hydrogen or an alkali metal atom, and $R^1$ and $R^2$ together may also be

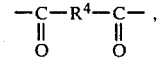

where $R^4$ is alkylene or

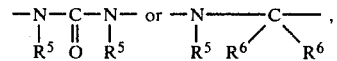

$R^5$ is hydrogen, chlorine or bromine and $R^6$ is an aliphatic radical, with an alkali metal hypochlorite in the presence of an alkali metal hydroxide at from 0° to 100° C., after which (b 3) the resulting mixture of 8-chloroisatoic anhydride of the formula

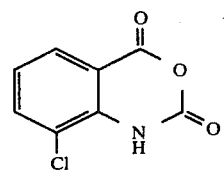

IIa and 5-chloroisatoic anhydride of the formula

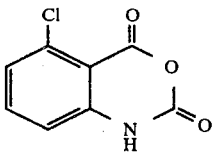

IIb is esterified with an alkanol of the formula

ROH                         III where R has the above meaning, in the presence of an esterification catalyst.

2. The process of claim 1, wherein the reaction is carried out with from 1 to 20 moles of ammonia or formamide per mole of phthalic anhydride.

3. The process of claim 1, wherein the reaction in stage b 1) is carried out at from 80° C. to 300° C.

4. The process of claim 1, wherein the reaction in stage a 1) or b 2) is carried out with from 0.9 to 1.5 moles of hypochlorite and from 0.9 to 3 moles of alkali metal hydroxide (not including the alkali contained in the hypochlorite), per mole of 3-chlorophthalic anhydride or 3-chlorophthalimide.

5. The process of claim 1, wherein the reaction in stage a 1) or b 2) is carried out in the presence of bromine, iodine and/or an amide of the formula

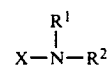

IV where $R^1$ is a sulfonic acid group, a sulfonate radical or a sulfonamide group, $R^2$ is hydrogen, an aliphatic radical, chlorine or bromine, X is chlorine, bromine or hydrogen, $R^1$ and $R^2$ may also, conjointly with the adjacent nitrogen, be members of a heterocyclic radical which contains, adjacent to the nitrogen, one or more sulfone groups or phosphonyl groups of the formula

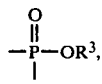

where $R^3$ is hydrogen or an alkali metal atom, and $R^1$ and $R^2$ together may also be

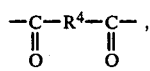

where $R^4$ is alkylene or

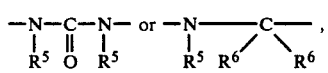

$R^5$ is hydrogen, chlorine or bromine and $R^6$ is an aliphatic radical, using from 0.0001 to 0.1 mole of 3-chlorophthalic anhydride or 3-chlorophthalimide.

6. The process of claim 1, wherein the reaction a 1) or b 2) is carried out at from 0° to 100° C.

7. The process of claim 1, wherein the reaction in stage a 1) gives a ratio of from 2.9 to 3.1 moles of 8-chloroisatoic anhydride per mole of 5-chloroisetoic anhydride or the reaction of stage b 2) gives a ratio of from 2.9 to 3.1 moles of 5chloroisatoic anhydride per mole of 8-chloroisatoic anhydride.

8. The process of claim 1, wherein the reaction in stage a 2) or b 3) is carried out with from 1 to 50 moles of alkanol III per mole of 5-chloroisatoic anhydride and 8-chloroisatoic anhydride.

9. The process of claim 1, wherein the reaction of stage a 2) or b 3) is carried out at from 10° to 170° C.

10. The process of claim 1, wherein the reaction of stage a 2) or b 3) is catalyzed with an acid.

11. The process of claim 1, wherein the reaction of stage a 2) or b 3) is carried out with from 0.5 to 15 percent by weight of an acid, based on starting materials IIa and IIb.

12. The process of claim 1, wherein the reaction of stage a 2) or b 3) is carried out with a base as the catalyst.

13. The process of claim 1, wherein the reaction of stage a 2) or b 3) is carried out with from 0.01 to 0.5 equivalent of basic compound per mole of starting materials IIa and IIb.

14. A process for the preparation of a mixture of an alkyl 3-chloroanthranilate of the formula

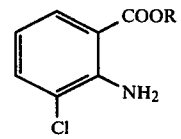

and an alkyl 6-chloroanthranilate of the formula

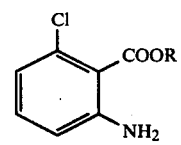

where R is alkyl, in a ratio of from 2.9 to 3.1 moles of the one ester to one mole of the other ester, wherein
(b 1) 3-chlorophthalic anhydride is reacted with formamide and thereafter
(b 2) the resulting 3-chlorophthalimide is reacted with an alkali metal hypochlorite in the presence of an alkali metal hydroxide at from 0° to 100° C., after which
(b 3) the resulting mixture of 8-chloroisatoic anhydride of the formula

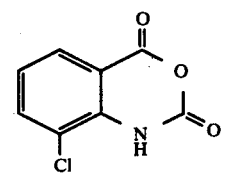

and 5-chloroisatoic anhydride of the formula

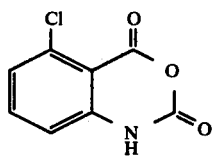

is esterified with an alkanol of the formula

ROH                                                III where R has the above meaning, in the presence of an esterification catalyst.

* * * * *

UNITED STATES PATENT AND TRADEMARK OFFICE
CERTIFICATE OF CORRECTION

PATENT NO. : 4,306,074
DATED : December 15, 1981
INVENTOR(S) : Peter Tonne, Heinz-Guenter Oeser and Dietrich Mangold It is certified that error appears in the above-identified patent and that said Letters Patent is hereby corrected as shown below:

Cover page of patent, the line following line [30], the date should read --Jun. 20, 1979-- not "Jun. 20, 1977".

Col. 13, line 28, after "mole" insert --of catalyst per mole--.

Signed and Sealed this

*First* Day of *November 1983*

[SEAL]

*Attest:*

*Attesting Officer*

GERALD J. MOSSINGHOFF

*Commissioner of Patents and Trademarks*